United States Patent [19]

Hinz

[11] Patent Number: 5,527,913
[45] Date of Patent: Jun. 18, 1996

[54] METHODS FOR PURIFYING CAMPTOTHECIN COMPOUNDS

[75] Inventor: Hellmuth R. Hinz, Kingwood, Tex.

[73] Assignee: The Stehlin Foundation for Cancer Research, Houston, Tex.

[21] Appl. No.: 200,398

[22] Filed: Feb. 23, 1994

Related U.S. Application Data

[63] Continuation-in-part of Ser. No. 22,091, Feb. 25, 1993, Pat. No. 5,352,709.

[51] Int. Cl.$^6$ .................................................. C07D 491/22
[52] U.S. Cl. ................................................ 546/48; 546/70
[58] Field of Search ..................................................... 546/48

[56] References Cited

U.S. PATENT DOCUMENTS

| | | |
|---|---|---|
| 3,894,029 | 7/1975 | Winterfeldt et al. . |
| 4,399,282 | 8/1983 | Miyasaka et al. ........................ 546/48 |
| 4,473,692 | 9/1984 | Miyasaka et al. ........................ 546/48 |
| 4,914,205 | 4/1990 | Sawada et al. . |
| 4,943,579 | 7/1990 | Vishnuvajjala et al. .................. 546/48 |
| 5,053,512 | 10/1991 | Wani et al. . |
| 5,180,722 | 1/1993 | Wall et al. . |

FOREIGN PATENT DOCUMENTS

| | | |
|---|---|---|
| 0538534 | 4/1993 | European Pat. Off. . |
| 56-108787 | 8/1981 | Japan . |
| 64-61482 | 3/1989 | Japan . |
| WO92/05785 | 4/1992 | WIPO . |
| 94-19353 | 9/1994 | WIPO .................................... 546/48 |

OTHER PUBLICATIONS

Akimoto et al., Journal of Chromatography, vol. 588, pp. 165–170, 1991.
Gunasekera et al., Journal of Natural Products (Lloydia), vol. 42, No. 5, pp. 475–477, 1979.
Sakato et al., Agricultural and Biological Chemistry, vol. 38, No. 1, pp. 217, 218, 1974.
Fessenden et al., Techniques and Experiments for Organic Chemistry, PWS Publishers, 1983, ISBN 0–8175–0755–2, pp. 56–59.
Van Nostrand's Scientific Encyclopedia 7th Ed. (vol. 1) (1989), pp. 625–627.
McGraw Hill Encyclopedia of Science & Technology, vol. 3, 5th Ed., 1982, pp. 142–146.
Wani et al., J. Med. Chem., vol. 23, pp. 554–560, 1980.
Wani et al., J. Med. Chem., vol. 29, pp. 2358–2363, 1986.
Wall et al., J. Med. Chem., vol. 29, pp. 1553–1555, 1986.
Wall et al. J. Med Chem vol. 29 pp. 1553–1555 (1986).
Barilero et al. Jour. Chromatog. vol. 575 pp. 275–280 (1992).
Akimoto et al. Jour. Chromotog. vol. 588 pp. 165–170 (1991).
Gunasekera et al. Jour. Nat. Prod. (Lloydia) vol. 42 No. 5 pp. 475–477 (1979).

*Primary Examiner*—Donald G. Daus
*Attorney, Agent, or Firm*—Finnegan, Henderson, Farabow, Garrett & Dunner

[57] ABSTRACT

Methods for purifying 20(S)-camptothecin are described. The 20(S)-camptothecin in purified form is useful in the treatment of cancer.

7 Claims, 8 Drawing Sheets

METHODS FOR PURIFYING CAMPTOTHECIN COMPOUNDS

PRIOR APPLICATION INFORMATION

This application is a continuation-in-part of application Ser. No. 08/022,091, filed Feb. 25, 1993, now U.S. Pat. No. 5,352,709 which is incorporated in its entirety herein by reference.

FIELD OF THE INVENTION

The present invention relates to methods for purifying 20(S)-camptothecin (also known as CPT).

BACKGROUND OF THE INVENTION

20(S)-camptothecin (CPT) is a natural alkaloid product which is present as a component in a crude plant material isolated from the Chinese tree *Camptotheca acuminata* (Nyssaceae) (Wall, M.; Wani, M. C.; Cooke, C. E.; Palmer, K. H.; McPhail, A. T.; and Slim, G. A., "Plant antitumor agents. I. The isolation and structure of camptothecin, a novel alkaloidal leukemia and tumor inhibitor from *Camptotheca acuminata*", *J. Am. Chem. Soc.* 88:3888–3890, 1966). CPT can also be isolated from the Indian tree *Mappie foetida Miers* (Govindachari, T. R. and Viswanathan, N., "Alkaloids of Mappia Foetida", *Phytochemistry* 11:3529–3531 (1972)). CPT has been determined to possess considerable antitumor activity (Wani, M. C. and Wall, M. E. "Plant Antitumor Agents. II. The Structure of Two New Alkaloids from *Camptotheca acuminata*", *J. Org. Chem.* 34(5):1364–1367 (1968) and has since been the focus of much scientific endeavor (See reviews: 1) Shamma, M.; St. Georgiev, V.; *Journal of Pharmaceutical Sciences* 63(2):163–183 (1974); 2) D'Arpa, P. and Liu, L. F. "Topoisomerases-targeting antitumor drugs" *Biochimica et Biophysica Acta.* 989:163177 (1989); 3) Corcoran, J. W. and Hahn, F. E. "Mechanism of Action of Antimicrobial and Antitumor Agents" *Antibiotics*, Vol. III, Springer-Verlag, New York, Heidelberg, Berlin, pp. 48–57 (1975); 4) Hutchinson, C. R. "Camptothecin: Chemistry, Biogenesis and Medicinal Chemistry", *Tetrahedron* 37:1047–1065 (1981); 5) Cai, J. C. and Hutchinson, C. R., "Camptothecin", *The Alkaloids*, Vol. XXV, pp. 101–137 (1983)). Recently, it was shown that CPT has high activity against human cancer xenografts in vivo (Giovanella, B. C.; Hinz, H. R.; Kozielski, A. J., Stehlin, Jr., J. S.; Silber, R. "Complete Growth Inhibition of Human Cancer Xenografts in Nude Mice by Treatment with 20(S)-camptothecin", *Cancer Research*, 51:3052–3055 (1991)), as well as in vitro (Pantazis, P.; Hinz, H. R.; Mendoza, J. T.; Kozielski, A. J.; Williams, Jr., L. J.; Stehlin, Jr., J. S.; Giovanella, B. C. "Complete Inhibition of Growth Followed by Death of Human Malignant Melanoma Cells In Vitro and Regression of Human Melanoma Xenografts in Immunodeficient Mice by Camptothecins," *Cancer Research*, 52:3980–3987 (1992)). It is of interest that a highly efficient method be developed for the purification of CPT since CPT is generally commercially available only as a plant extract.

The traditional methods of purifying CPT involve the use of conventional chromatography using a mixture of solvents, usually a nonpolar solvent in conjunction with a polar solvent to affect the separation of individual molecules from each other with silica gel, followed by crystallization from methanol-acetonitrile. (Wall, M. E., Fourth International Symposium on the Biochemistry and Physiology of Alkaloids, Halle, DDR, Jun. 25–28, 1969, pp. 77–87; Wall et al. 1966, supra.)

SUMMARY OF THE INVENTION

An object of the present invention is to provide novel methods for purifying 20(S)-camptothecin, preferably from naturally occurring sources.

Additional objects and advantages of the present invention will be set forth in part in the description which follows, and in part will be apparent from the description, or may be learned by practice of the present invention. The objects and advantages of the present invention will be realized and attained by means of the elements and combinations particularly pointed out in the appended claims.

To achieve the objects and in accordance with the purpose of the present invention, as embodied and broadly described herein, the present invention relates to a method of purifying 20(S)-camptothecin comprising the steps of (1) charging a column with an absorbent compound and wetting the compound with a solvent; (2) passing a solvent containing a starting material containing CPT through the column; (3) eluting the column with a solvent, whereby components of the starting material containing CPT both more polar and less polar than the CPT are eluted and wherein the solvent in steps (1), (2) and (3) can be the same or different; (4) eluting the column with a solvent more polar than the solvent(s) in steps (1), (2) and (3); and (5) separating the CPT from the eluent resulting from the elution in step (4) to obtain the purified CPT.

Further, the present invention relates to a method of purifying 20(S)-camptothecin comprising the steps of: (1) heating under reflux a mixture of a starting material containing CPT and an excess amount of acetic acid and/or propionic acid under conditions whereby a solution mixture free of oxygen is formed; (2) adding HBr, HCl or a mixture thereof to the solution mixture in an effective amount and continuing said heating under reflux until the starting material containing CPT is dissolved to form a solution; (3) monitoring the heating under reflux by means of thin layer chromatography and continuing the heating until a material immediately following CPT on a thin layer chromatography plate has disappeared; (4) removing plant and decomposition products from the solution; and (5) separating CPT from the solution by crystallization to obtain the purified CPT.

Also, the present invention relates to a method of purifying 20(S)-camptothecin comprising the steps of: (1) derivatizing a starting material containing CPT to a substituent on the $C_{20}$-hydroxyl group thereof; (2) purifying the derivative; and (3) converting the derivative back to CPT to obtain the purified CPT.

In addition, the present invention relates to a method of purifying 20(S)-camptothecin comprising the steps of: (1) combining an aqueous base containing an hydroxide ion, a water immiscible organic solvent, and a starting material containing CPT to form a mixture having an aqueous phase and an organic phase; (2) separating the organic phase from the aqueous phase; (3) acidifying the aqueous phase to form CPT crystals; and (4) separating the crystals obtained in step (3) to obtain the purified CPT.

It is to be understood that both the foregoing general description and the following detailed description are exemplary and explanatory only and are not restrictive of the present invention, as claimed.

DETAILED DESCRIPTION OF THE PREFERRED EMBODIMENT(S)

Figure 1A:
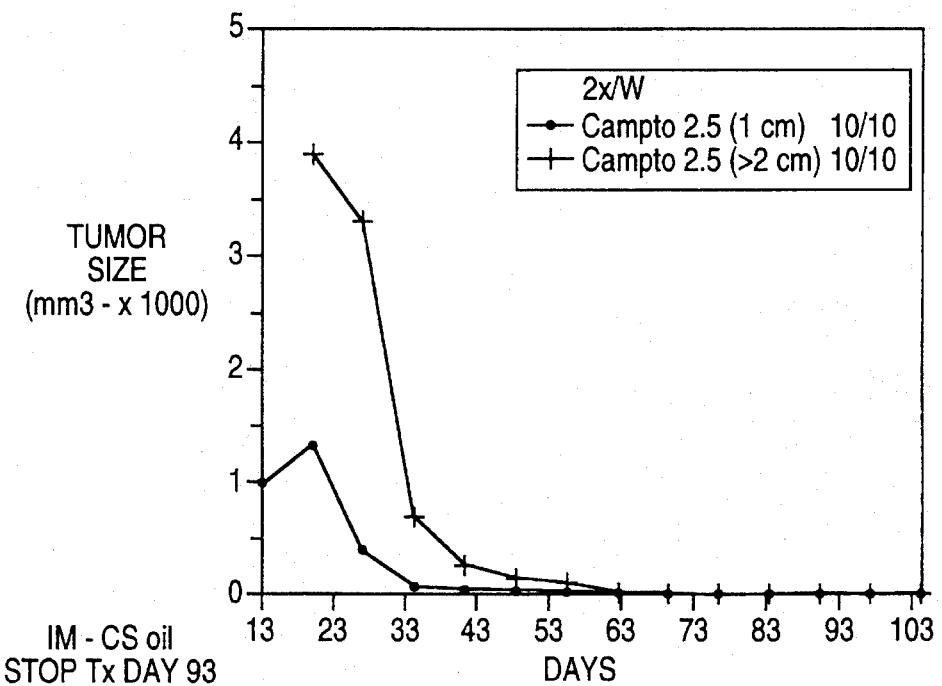
FIGS. 1a and 1b show the effectiveness of CPT purified in accordance with the present invention when administered intramuscularly against human breast cancer.

20(S)-camptothecin (CPT) is an alkaloid component of a crude plant material isolated from *Camptothera acuminata*. The crude plant material can be obtained, for instance, from the Institute of Materia Medica, Academia Sinica, Shanghai, China, or Sigma Biochemicals, or Good Land Enterprises, Vancouver, Canada.

The natural plant material—regardless of its source—does not contain only CPT, but also other natural products, e.g. derivatives of CPT, which have to be separated from CPT. For instance, the plant material has also the presence of 10-hydroxy-20(S)-CPT, 10-methoxy-20(S)-CPT, 11-hydroxy- 20(S)-CPT and 11-methoxy-20(S)-CPT (Wani, M.C. and Wall, M. E., 1968) and also 20-deoxycamptothecin ((a) Hsu, J.-S.; Chao, T.-Y.; Lin, L.-T.; Hsu, C.-F., Hua Hsueh Hsueh Pao 1977, 35:193; *Chem. Abstr.* 1979, 90:28930; (b) Adamovics, J. A.; Cina, J. A.; Hutchinson, C. R. Phytochemistry, 18:1085 (1979); (c) Lin, L.-T.; Sung, C.-C.; Hsu, J.-S., K'o Hsueh Tung Pao, 24(10:478-479 (1979); *Chem. Abstr.* 1979, 91:193482u) in the starting material containing CPT from *camptotheca acuminata*. The starting material containing CPT may also contain 9-methoxy-20(S)-CPT and mappicine, if the source of the material is Mappia Foetida Miers (Olacaceae) (Govindachari, T. R. and Viswanathan, N., "9-Methoxy camptothecin. A New Alkaloid from *Mappia foedia Miers*", *Indian Journal of Chemistry*, 10(1):453-454 (1972); and Govindacharie, T. R.; Ravindranath, K. R.; Viswanathan, J. "Mappicine, a Minor Alkaloid from *Mappia foetida Miers*"), 10-methoxy-20(S)-CPT, if the source is *Ophiorrhiza mungos* (Rubiaceae) (Tafur, S.; Nelson, J. D.; DeLong, D. C.; Svoboda, G. H. "Antiviral Components of Ophiorrhiza mungos—Isolation of Camptothecin and 10-Methoxycamptothecin" Lloydia 39:261-262 (1976)), or 9-methoxy-20(S)-CPT if the source is ervatania heyneana (Gunasekera, S. P.; Badawi, M. B.; Cordell, G. A.; Farnsworth, N. R.; Chitis, M. "Plant Anticancer Agents X. isolation of Camptothecin and 9-Methoxycamptothecin from Ervatamia Heyneana", *Journal of Natural Products*, 42(5):475-477 (1979)).

It is to be understood that the term "starting material containing CPT" as used herein refers to the impure source containing CPT, crude CPT, CPT plant extract, any plant material containing CPT, synthetic CPT, reaction products containing CPT, and any CPT-containing material wherein the CPT present therein is isolated in purified form by any one of the methods of the present invention. It is also further understood that purified CPT as used herein means CPT isolated in purified form by one of the methods of the present invention wherein the recovered CPT has a purity greater than the purity of the starting material containing CPT. CPT obtained from plant extracts generally has a purity of 60% or greater. The methods of the present invention are generally effective in isolating and purifying CPT to final purity levels of about 95% or higher.

Thus, CPT, in order to be used in anticancer activity should be extensively purified prior to administering because: (1) the natural product contains several other components which contribute to a large degree of toxicity, for example in mice, and (2) FDA regulations require such purifying for any drug or compound.

It will be apparent to those skilled in the art that various modifications and variations can be made in the methods of the present invention without departing from the spirit or scope of the invention. Thus, it is intended that the present invention cover the modifications and variations of this invention provided they come within the scope of the appended claims and their equivalents.

Method I: Purification of CPT by Means of Column Chromatography

In this method, a column, such as any commercially available chromatography column, for example, columns made by Ace Glass or Fisher Scientific, having for example the dimensions 5×90 cm, but may be smaller or larger, depending on the amount of material to be chromatographed, is charged with a solvent along with an adsorbent compound, e.g., a silica gel, alumina, magnesium silicate, magnesia, carbon, diatomaceous earth, porous beads, and special adsorbents or a combination thereof obtained for example from Aldrich or Sigma. Any column may be used which allows the adsorbent to be packed inside the column (composed of plastics, Pyrex® or other forms or glass or glass-like materials, pure metals or suitable alloys of metals or alloys of metals with nonmetals, steel or stainless steel or a suitable combination thereof known and understood by those skilled in the art) in a fashion such that the sample to be chromatographed may be introduced at one end of the adsorbent and then separated into one or more individual components and eluting through the other end of the column by flowing solvent through the packed adsorbent. This process may be carried out at low pressures (less than one atmosphere) up to very high pressures of several thousand atmospheres of pressure known to those skilled in the art, including, but not limited to, HPLC. The separation may also be carried out at normal room temperature or higher for example, 100° C., or lower for example, 0° C., temperatures. A preferred solvent is $CH_2Cl_2$. Other solvents can also be used, such as ethers, e.g. diethyl ether, hexanes, pentanes, $CHCl_3$ and mixtures thereof.

The adsorbent, e.g. silica or alumina, which is used generally has a size of 70–270 mesh. Other grades may also be used. As known in the art, the amount of solvent and the adsorbent is directly related to the size of the column which is used for the purification. For example, in a column having the dimensions 5×90 cm, approximately 200 ml of adsorbent is used.

Starting material containing CPT is stirred into a solvent which contains an adsorbent. Optionally, a little sand may be added to the top of the adsorbent, such as silica gel, after the adsorbent settles. After the adsorbent settles, substantially all of the solvent is decanted and more solvent is added almost to the top of the adsorbent bed and sand line, if sand is used. The adsorbent containing most of the CPT is then added to the top of the column, followed by the supernatant liquid containing the rest of the starting material containing CPT.

Generally, for every 1000 ml of solvent, for example $CH_2Cl_2$, used, approximately 150 ml of absorbent are used.

Upon adding the starting material containing CPT in the solvent, the column is then developed or eluted with fresh solvent which can be the same or different from the solvents used initially and discussed above, for example, $CH_2Cl_2$.

The progress of the column development can be monitored by such techniques as thin layer chromatography (TLC), which uses, for example, a two to three percent concentration of $CH_3OH$ in $CHCl_3$. Other suitable elution mixtures for use in TLC are known by those skilled in the art.

In this method, it is most remarkable to note that not only the less polar material clears the column before the more polar CPT, but also that other components, which are more polar than CPT, actually surpass CPT and clear the column before CPT does. After the clearance of these less polar and more polar components, CPT may then be retrieved by the addition and elution with a solvent or mixture of solvents more polar than the solvent(s) used. Examples of such polar solvents include methanol, ethanol, propanol, isopropanol and so forth. Thus, the purified CPT is retrieved by eluting the column with a polar solvent.

The purified CPT in the solution may then subsequently be recrystallized by various known methods to those skilled in the art such as slow evaporation of the solvent which contains the purified CPT. Another means of recrystallization which is part of the present invention is the recrystallizing from N,N-dimethylacetamide (DMA), or any other suitable medium that has the ability to bind or interact acidic hydroxyl hydrogens. Further, an additional recrystallization step can be used wherein the recrystallization is from acetic acid/ethanol by dissolving the crystals in hot acetic acid and then adding ethanol as described in method II below, which at this point removes further impurities from the crystals.

The manner in which CPT behaves with regard to movement on silica or alumina in the solvent medium described above contributes to the ease of purification of not only CPT, but also the efficient isolation of the various other components present in the plant material.

Method II: Isolation of CPT Chemical Treatment and Recrystallization for Large Quantity Purification of CPT In this method, an excess amount of acetic acid and/or propionic acid (or other suitable alkyl group (e.g. $C_1$–$C_6$) containing carboxylic acids) is charged into a container, such as a round bottom flask with a starting material containing CPT. Generally, for every 100 grams of starting material containing CPT, 2500 ml of acetic acid and/or propionic acid (i.e., an excess amount) are used. Upon charging the acetic acid and/or propionic acid and starting material containing CPT into the container, oxygen is removed therefrom, such as by heating the mixture to about 100° C. for approximately one hour under a continuous stream of an inert gas, such as nitrogen. After this point, HBr, HCl or a mixture thereof is added to the container. For example, 100 ml of 48% aqueous HBr and 200 ml concentrated HCl can be used.

The mixture is heated, generally for about six hours. Though not necessary, it is preferred that when the temperature reaches approximately 100° C. during heating, another aliquot of HBr, HCl or a mixture thereof, e.g. 50 ml HBr, is added to the solution and the heating is continued until all of the starting material containing CPT is dissolved.

At this point, the temperature of the solution may be approximately 106° C. during this continuing refluxing. The heating is continued until the material immediately following the CPT (backspot) on a TLC plate (using a mixture of 3% $CH_3OH$: $CHCl_3$ as the eluant for example) has disappeared. Typically, in a preferred 3% $CH_3OH$:$CHCl_3$ system, the frontspot has an $R_f$ value of 0.7. The "backspot" has an $R_f$ value of 0.6 and the phenolic 10-hydroxy CPT, 9-hydroxy CPT or 11-hydroxy CPT has an Rf value of 0.1.

Afterwards, purified CPT is separated from the solution. In one preferred embodiment, water is added to the solution. Generally, approximately 350 ml of water per 2500 ml of acetic acid are added to the solution. Upon adding water, though not necessary, it is preferred that the solution be placed in a lower temperature atmosphere such as a refrigerator for about 12 hours.

Afterwards, the solution is filtered by means known in the art. Such filtering can be accomplished, for example, by a buchner funnel with a small fritt pore to remove plant and decomposition products from the solution, or by using a filter aid such as Celite®. To the resulting supernatant liquid, ice-water is added which results in the LAW OFFICES crystallization of purified CPT which may be collected on a further filtering device, such as a buchner funnel. The crystals may then be washed, for instance, with water, until the wash is no longer acidic to pH paper. The crystals are then broken up and dried overnight in a vacuum by, for example, applying a vacuum of approximately 0.1 atmosphere and heating the crystals to about 50° C. Alternatively, the crystals may be allowed to air dry, preferably in a fume hood.

At this point, as judged, for example, by TLC, the crystals may still contain some of the more polar phenolic compounds and other less polar compounds. The phenolic compounds may be removed by recrystallization from N,N-dimethylacedemine (DMA) (or any other suitable medium that has the ability to remove the acidic hydroxyl hydrogen-containing compounds like 9-, 10- or 11-hydroxy CPT).

A further step in the purification may be another recrystallization from acetic acid/ethanol (the composition of this mixture is described in Example 2 infra.), which at this point, removes the less polar materials from the crystals.

Trituration from absolute ethanol yields slightly yellow CPT after filtration, which is analytically pure on TLC and has a minimum purity of 98% as established by HPLC and $^1$H-NMR. The supernatant liquid may be concentrated in vacuo and the resulting crystals may be re-recrystallized to obtain a further crop of CPT. The quantities purified by this method may be scaled up indefinitely and, thus, are only limited by the size of the reaction vessels.

Method III: Purification of CPT by Chemical Derivatization Followed by Isolation of the Derivative and the Subsequent Reconversion to CPT Another route of chemical modification/isolation of CPT is to first convert CPT to a more soluble and better behaved molecule. This is easily achieved by transforming CPT into a derivative, which has a much better solubility than CPT, and therefore makes it much easier to isolate by standard purification procedures. Such a modification of CPT may be carried out at the $C_{20}$-hydroxyl group, by converting CPT into a derivative for instance, an ester or ether. One such derivative may be for example an acetate like the one described by Wall et al. (1966) supra., or any other, as long as the goals are accomplished, for instance, greater solubility in organic solvents combined with a relatively easy reconversion of the derivative back to CPT. An ester or ether with these properties is easily obtainable and purifiable by any of the usual chromatographic procedures known to those skilled in the art, such as the procedure used in Example 3, infra.

After the ester or ether is purified by removal of most of the impurities, the ester or ether may be hydrolyzed by any number of hydrolysis methods known to those skilled in the art to give back CPT in a pure form. This may be accomplished, for example, by heating the respective ester or ether in aqueous sulfuric acid or acetic acid in the presence of HCl and/or HBr as set forth in Example 3, infra. After the reconversion is complete, the CPT is recrystallized by the method using acetic acid/ethanol as described earlier in method II.

It should be pointed out that many different derivatives may be synthesized by modification of the $C_{20}$ hydroxyl group. This derivative is not at all limited to esters or ethers, although esters are preferred.

The same holds true for the hydrolysis of the derivative to yield back CPT in a purified form. Many different media, including organic and inorganic acids and bases can be used in this hydrolysis step.

Method IV: Purification of CPT by Converting the Lactone Ring to the Carboxylate Salt, Followed by Removal of By-Products and Reconversion to Natural CPT Another method which works quite effectively involves the chemical modification of the lactone ring system in CPT. The lactone ring is labile under basic conditions, allowing it to be readily converted to its corresponding carboxylate salt by treatment with an aqueous base, e.g. one containing an hydroxide ion, which allows the effective conversion and extraction of CPT into an aqueous system. Examples of aqueous bases include alkali metal hydroxides where the metal is preferably monovalent, for instance, potassium, lithium, or sodium.

In particular, in this method a water immiscible organic solvent, an aqueous base and a starting material containing CPT are combined to form an aqueous phase containing the CPT and an organic phase. The organic solvent, for example, can be chloroform, methylene chloride, or carbon tetrachloride or mixtures thereof. By conducting this chemical derivatization, most of the other natural products and plant products are removed by being retained in the organic phase.

After separating the CPT-containing aqueous phase, by means known to those skilled in the art e.g., separatory funnel, reconversion of the salt form of the CPT to the CPT having the lactone ring may be accomplished by reacidification of the aqueous layer with an acid. This acidification closes the lactone ring. Preferred acids include, for example, HCl, acetic acid, $H_2SO_4$, HI or mixtures thereof. Upon reacidification, isolation of the original, native form of CPT can be accomplished. Successive recrystallizations of the CPT material as discussed above yields the same pure material as stated earlier.

The present invention will be further clarified by the following Examples, which are intended to be purely exemplary of the present invention.

EXAMPLE 1

A column obtained from Ace Glass (5×90 cm) was charged with a nonpolar solvent, $CH_2Cl_2$ and 200 ml of silica of 70-270 mesh. Starting material containing CPT (10 gm) recorded as 93% CPT pure was stirred into a solution containing 1000 ml $CH_2Cl_2$ and 150 ml of silica gel. After settling, substantially all the solvent was decanted. The silica containing most of the CPT was added to the top of the column, followed by the supernatant solution containing the rest of the CPT. The column was then developed with pure $CH_2Cl_2$. The progress of the development of the column was monitored by TLC, which used a two to three percent concentration of $CH_3OH$ in $CHCl_3$. Not only the less polar materials cleared the column before CPT, but also the other components, which were more polar than CPT on silica, actually surpassed the CPT and cleared the column before the CPT. After the clearance of these less polar and more polar components, CPT was eluted when a polar solvent, methanol, was added to the $CH_2Cl_2$.

The yield as a result of this purification method was 4 gm. The purity was 99% by TLC.

EXAMPLE 2

In a well ventilated fume hood, a 5000 ml round bottom flask was equipped with a reflux condenser, nitrogen inlet and thermometer and charged with 2500 ml of acetic acid and 100 gm of starting material containing CPT (recorded as 93.7% CPT) obtained from Good Land Enterprise, Vancouver, Canada, and heated for one hour under a continuous stream of nitrogen in order to flush most of the oxygen out of the solution. After this point, 100 ml of 48% aq. HBr and 200 ml conc. HCl were added and the reaction mixture was heated for 6 hours, after which another aliquot of 50 ml HBr was added to the refluxing mixture. The temperature was monitored and when it reached approximately 100° C., another aliquot of 50 ml HBr was added to the solution and heating was continued until all the CPT dissolved. At this point the temperature of the solution was approximately 106° C. The heating was continued until the material immediately following CPT on a TLC plate (using a mixture of 3% $CH_3OH:CHCl_3$ as the eluant) disappeared. At this point 350 ml of $H_2O$ was added and the solution was put into a refrigerator for about 12 hours. The solution was then filtered through a large buchner funnel with a small fritt pore in order to remove plant and decomposition products from the solution. 2000 ml of ice-water were then added to the supernatant liquid and after refrigerating the mixture overnight, the resulting crystals were collected on a buchner funnel and washed with a large amount of water until the wash was no longer acidic.

The resulting CPT product was then recrystallized as follows.

To one gram of this CPT-product mixture 15 ml of DMA were added to a beaker wrapped with thermoinsulating material. This mixture was magnetically stirred and heated to 140°-145° C. during which the CPT material went into the solution. The solution was filtered hot through a buchner funnel and allowed to cool slowly to room temperature and then put into the refrigerator. The crystals formed in this manner were collected on a buchner funnel and the material was re-recrystallized using 13 ml of DMA until the orange color phenolic material disappeared on TLC when checked with a 3% CH₃OH:CHCl₃ solvent system. The yield was 65% CPT.

The crystalline material obtained in this fashion was re-recrystallized from acetic acid: ethanol to remove the less polar material in the following manner: One gram of this CPT was put into a flask and 28 ml of acetic acid was added and the mixture was heated until all the CPT was dissolved. At this point, 13 ml of ethanol were slowly added and the solution was then allowed to cool to room temperature very slowly to enhance the crystal purity. This step is repeated if the TLC system (3% CH₃OH:CHCl₃) still shows presence of this less polar front spot. The yield of CPT was 0.46 gm and the purity was 99%.

EXAMPLE 3

20 gm of starting material containing CPT (recorded as 93% CPT pure) were added under an inert atmosphere to 400 ml of pyridine catalyst at 0° C. and 23 ml of acetic anhydride. The solution was stirred for an hour at this temperature and then allowed to reach room temperature. The reaction was monitored by thin layer chromatography (TLC) using 3% methanol: chloroform as the eluant. After completion of the reaction, the pyridine was removed in vacuo, and approximately 50 ml of ice and 200 ml of methylene chloride were added to create organic and aqueous phases. The organic phase of the solution was separated and then washed with 1N HCl, followed by water and dried with anh. Na₂SO₄ sulfate. The organic phase of the solution was then adsorbed onto a column with silica and an elution was carried out with CH₂Cl₂. All of the less polar fractions and the one backspot component immediately trailing CPT were removed as described in method I. After removal of these compounds the polarity of the solvent was changed to 3% MeOH: CH₂Cl₂. Approximately 17 gm of acetate were obtained by this method contaminated with a little CPT. Hydrolysis was carried out by heating, under nitrogen atmosphere, one gram of the acetate with 10 ml 40% HBr and 5 ml H₂O. The reaction progress was monitored by TLC and after two hours, the reaction was complete. The mixture was cooled and 80 ml water was added to precipitate all the CPT out of the solution. The crystals were washed with water to remove all the hydrobromic acid followed by recrystallization from acetic acid: ethanol as described in method II. The yield of CPT was 0.9 gm and the purity was 99%.

EXAMPLE 4

1 gm of crude plant extract obtained from Good Land Enterprises (Vancouver, Canada) (recorded as 93% CPT) was added to 150 ml of CHCl₃ and 50 ml of 1% NaOH at low temperature (−5° C. to 0° C.). The mixture was stirred for 60 to 120 minutes at this temperature. The solution was filtered through a buchner funnel containing a bed of Celite® and transferred to a separatory funnel. The aqueous phase was separated and the organic phase was shaken once with 10 ml of ice cold 1% NaOH. The aqueous phases were then combined and washed once with 10 ml CHCl₃ and acidified slowly with ice cold 6M HCl and allowed to stand in the refrigerator. The resulting precipitate was filtered off. The yellow material was free of the backspot. The yield was 0.91 grams and the purity was less than 99%. As outlined in method II, this material was recrystallized from 20 ml DMA followed by re-recrystallization from acetic acid:ethanol. The yield was 0.44 grams and purity was 99%.

In order to show how the purified CPT of the present invention can be used, for example, in anti-cancer activity, the following example was conducted.

EXAMPLE 5

Swiss nude mice of the NIH high fertility strain were bred and maintained pathogen-free in the laboratory of the Stehlin Foundation. (Giovanella, B. C. and Stehlin, J. S. "Heterotransplantation of human malignant tumors in 'nude' thymusless mice. I. Breeding and maintenance of 'nude' mice." *J. Natl. Cancer Inst.* 51: 615–619; 1973.)

Human malignant carcinomas of the colon, breast, lung, ovary, stomach, and malignant melanomas were heterotransplanted directly from a patient into the nude mice and passaged serially. In particular, the tumors CLO, MUR, CAS, SW 48, SQU and BRO as described in Giovanella, B. C., Stehlin, J. S., Shepard, R. C. and Williams, L. J. "Correlation between response to chemotherapy of human tumors in patients and in nude mice." Cancer 52: 1146–1152; 1983), and tumor SCH as described in Heim, S., Mandahl, N., Arheden, K., Giovanella, B. C., Yim, S. O., Stehlin, J. S., Jr. and Mitelman, F. "Multiple karyotypic abnormalities including structural rearrangements of 11P in cell lines from malignant melanomas." *Cancer Genet. Cytogent.* 35: 5–20; 1988, and Verschraegen, C., Giovanella, B. C., Mendoza, J. T., Kozielski, A. J. and Stehlin, J. S., Jr. "Specific organ metastases of human melanoma cells injected into the arterial circulation of nude mice." *Anticancer Res., In Press* were used. Tumors CLO (Breast Carcinoma), BOL (Bladder Carcinoma), PC-3 (Prostate Carcinoma), BM #3 (Leukemia), WIL (Colon Carcinoma), TEP (Osteosarcoma), LOV (Pancreatic Carcinoma), BRO (Melanoma) were heterotransplanted. For the experiments, the tumor tissue was finely minced in complete MEM medium and 0.5 ml of a 10% v/v suspension was inoculated subcutaneously on the upper back of groups of 10–30 mice. When the tumors became palpable and measurable in all the animals, they were divided into groups of 4–8 and treated with the desired dose of the drug in experiment or with the vehicle only for the controls.

CPT purified by method II was prepared for i.m. injection or oral administration using cottonseed oil for example which included the dispersion of the test compound by sonication at 60° C. for 1 hour at the standard concentration of 0.25 to 1 mg/ml using an Ultrasonic Processor, Model 2200 by Branson Ultrasonics Corp., Danbury Conn. 06810-1961. Intramuscular injections were performed through a 27-gauge needle into the deep muscles of the posterior legs of the mice twice a week. The animals received up to 70 such injections consecutively without suffering ill effects except for some local fibrosis.

Figure 1B:
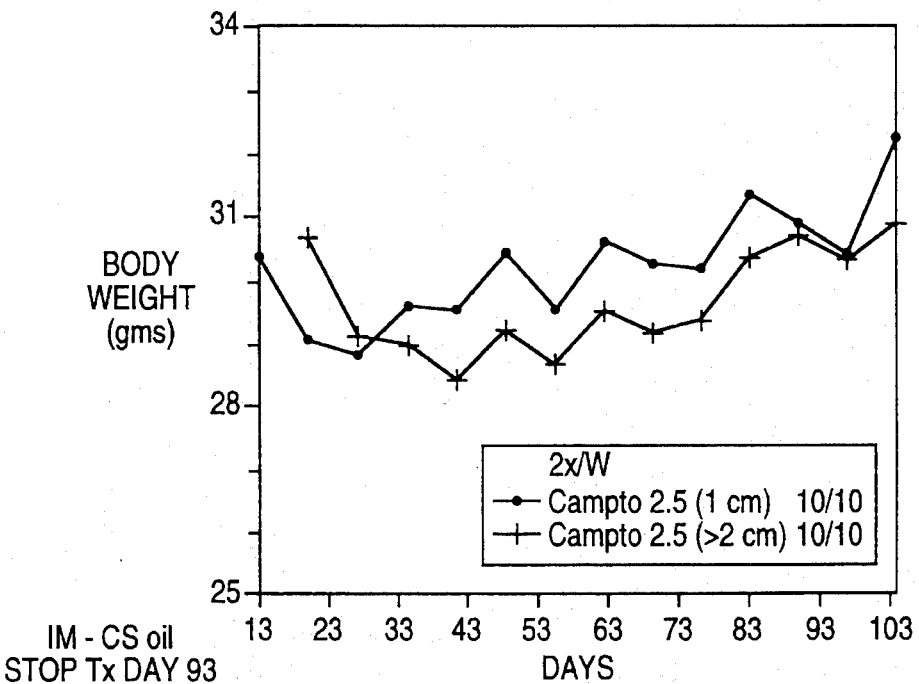
Figure 2A:
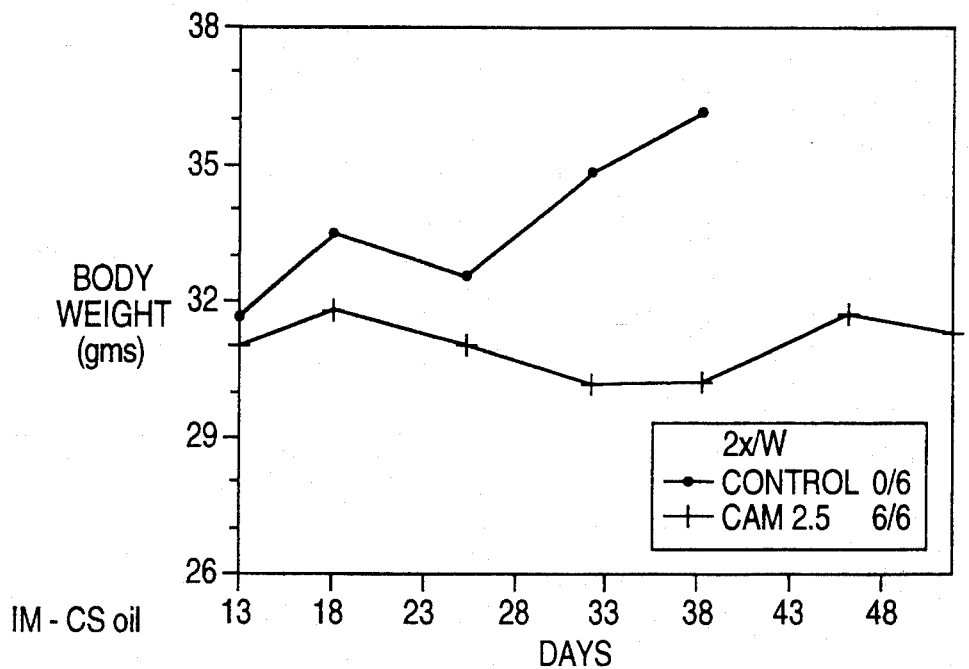
FIGS. 2a and 2b show the results obtained by treating a human bladder cancer xenograft by intramuscular administration of CPT purified in accordance with the present invention.
Figure 2B:
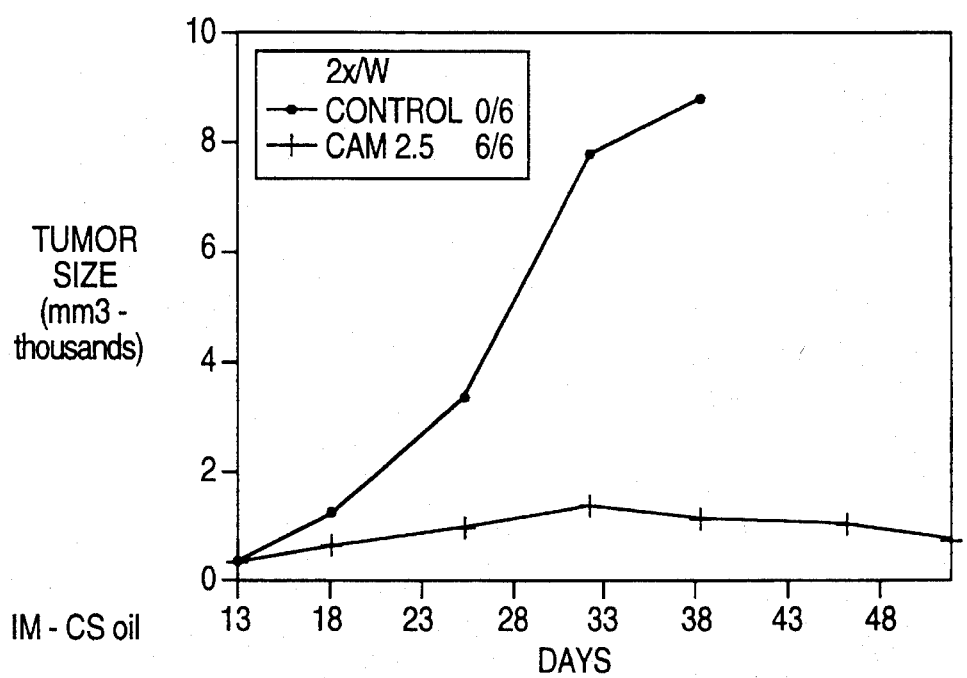

Oral administration was achieved by injecting the required amounts of drugs suspended in cottonseed oil directly into the stomach. FIGS. 1a and 1b show the effectiveness of CPT purified by one method of the present invention against the human breast cancer when administered intramuscularly, showing that even prolonged intramuscular administration of the compound of the present application do not have any effect on the body weight of the mice at the dosage of 2.5 mg/kg using cottonseed oil as the carrier. FIGS. 2a and 2b show the results obtained by treating a human bladder cancer xenograft by intramuscular administration of CPT purified by one method of the present invention.

Figure 3A:
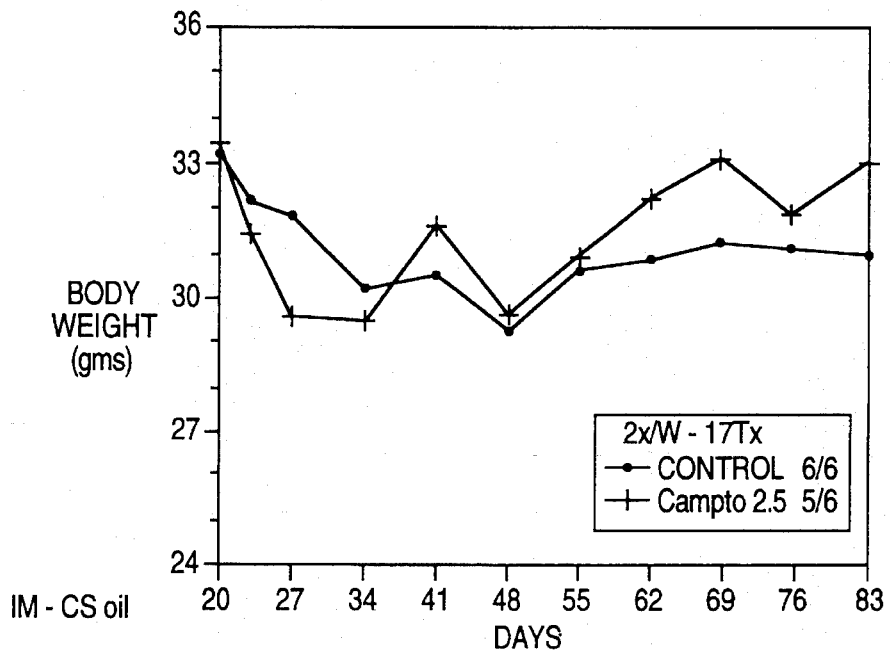
FIGS. 3a and 3b show the same results for human prostate cancer.
Figure 3B:
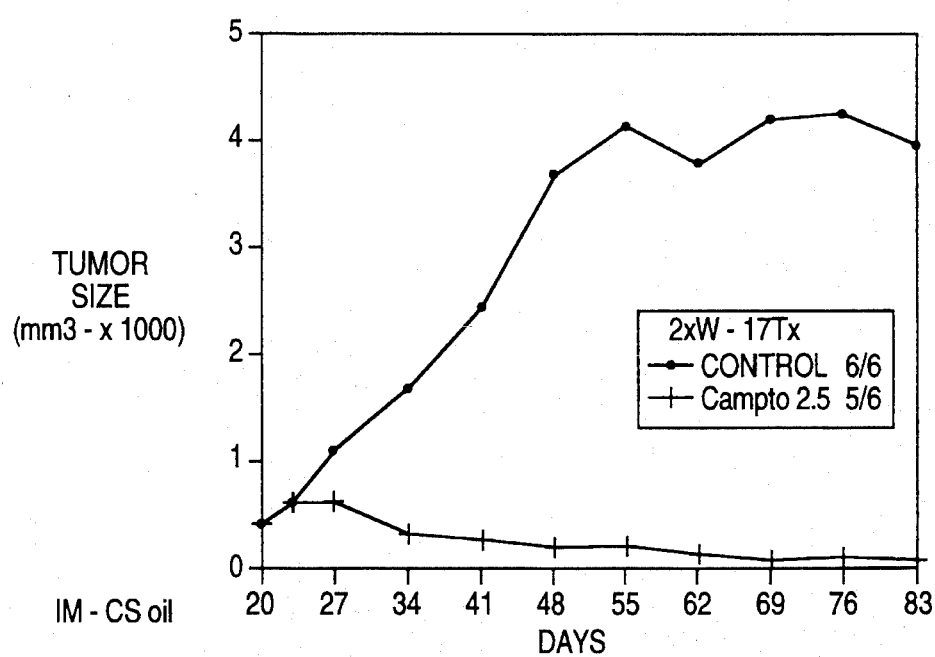

FIGS. 3a and 3b show the same results for human prostate cancer.

Figure 4A:
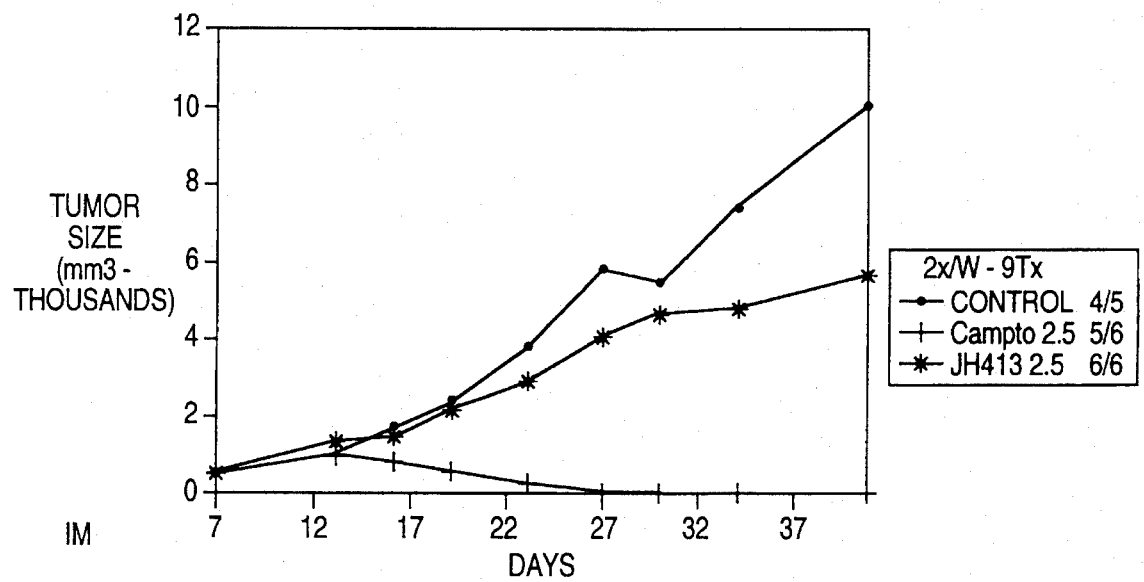
FIGS. 4a and 4b show the same results for human leukemia.
Figure 4B:
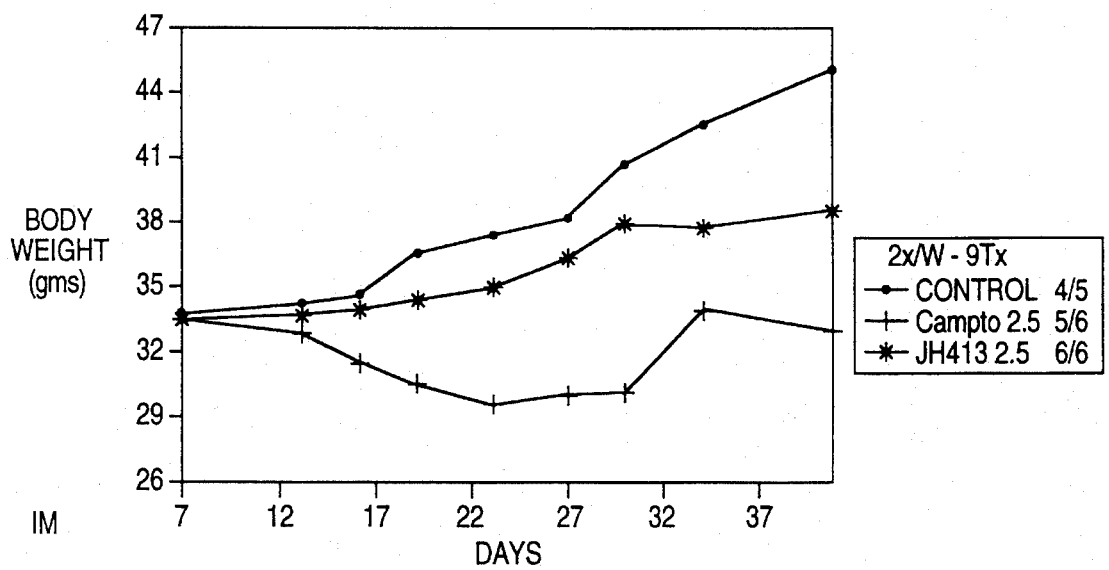

FIGS. 4a and 4b show the same results for human leukemia.

Figure 5A:
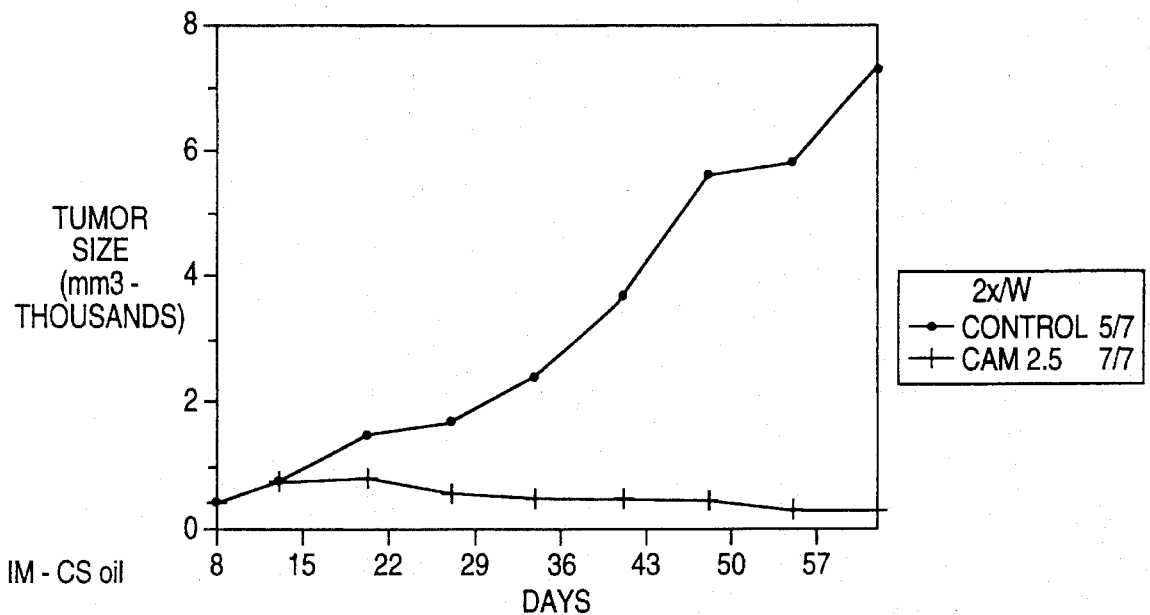
FIGS. 5a and 5b show the same results for human colon cancer.
Figure 5B:
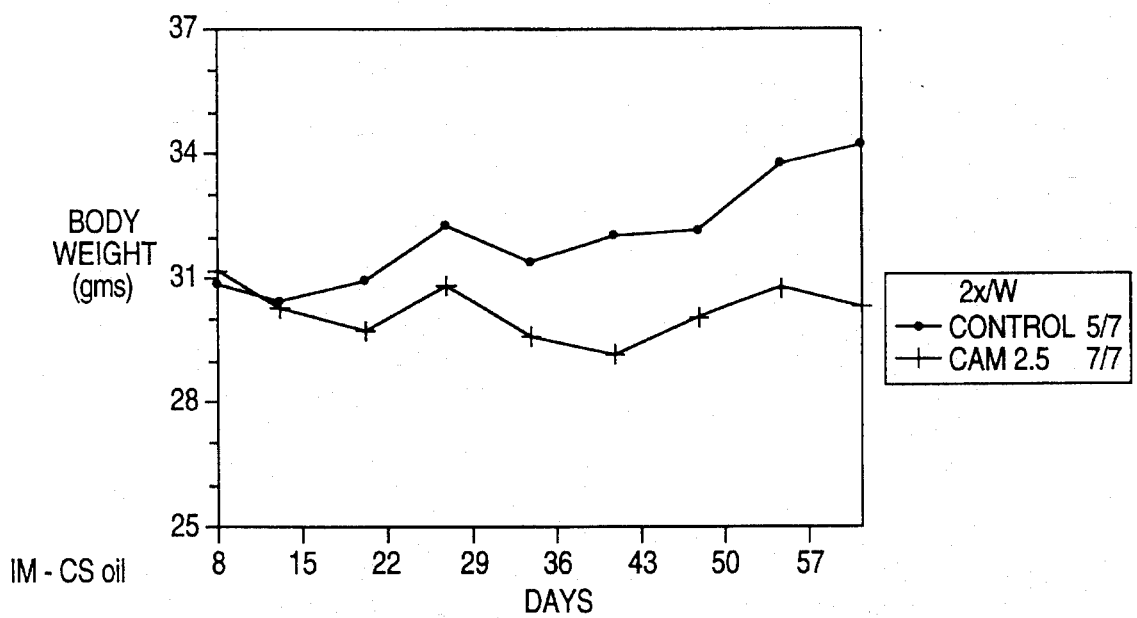

FIGS. 5a and 5b show the same results for human colon cancer.

Figure 6A:
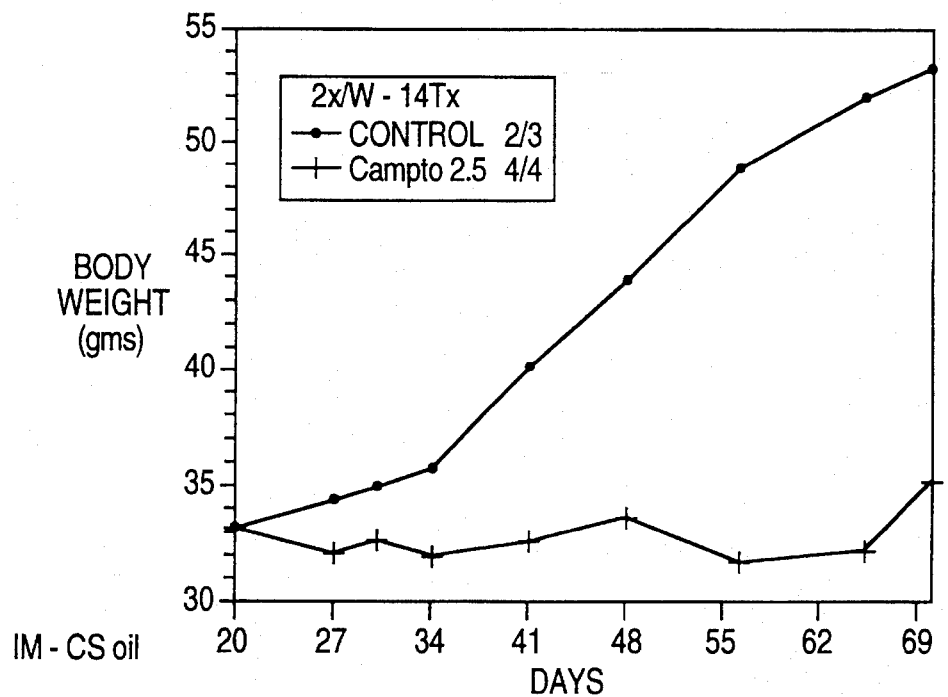
FIGS. 6a and 6b show the same results for human osteosarcoma.
Figure 6B:
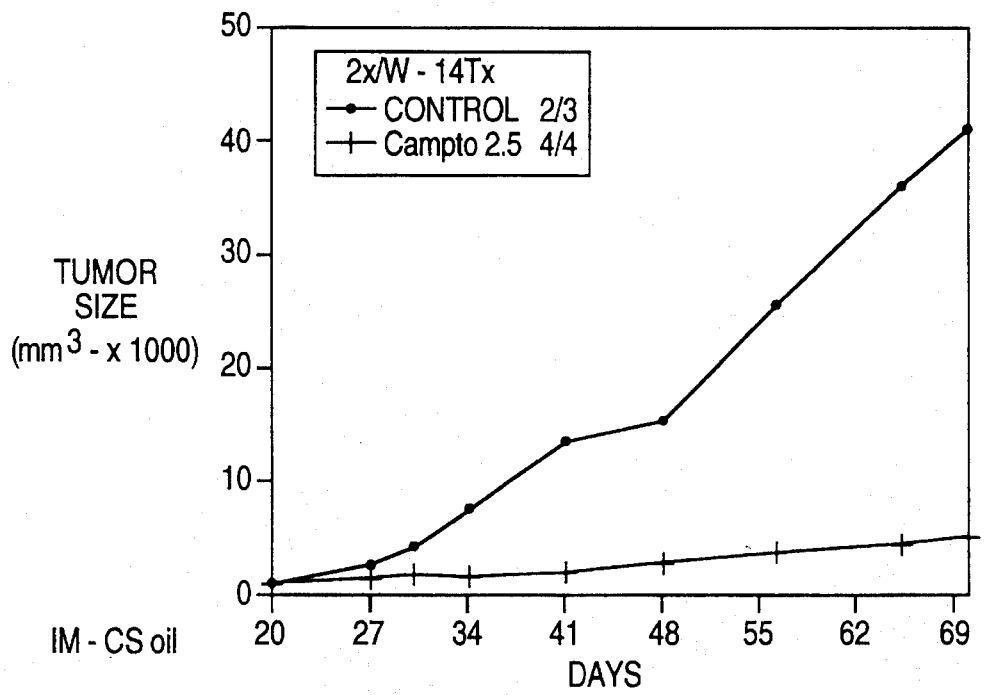

FIGS. 6a and 6b show the same results for human osteosarcoma.

Figure 7A:
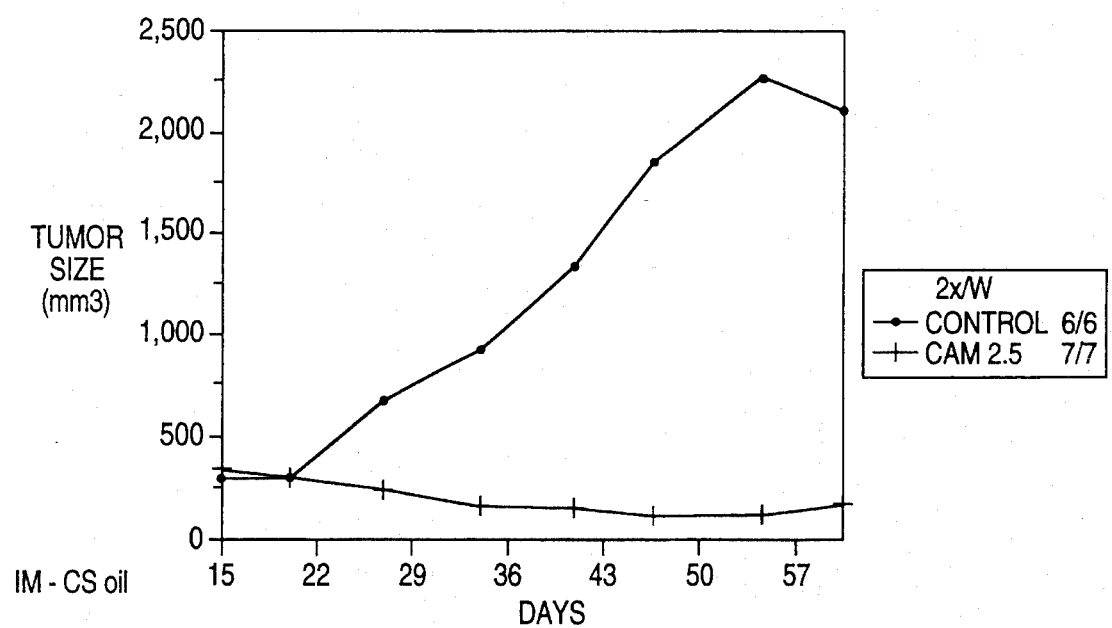
FIGS. 7a and 7b show the same results for human pancreatic cancer.
Figure 7B:
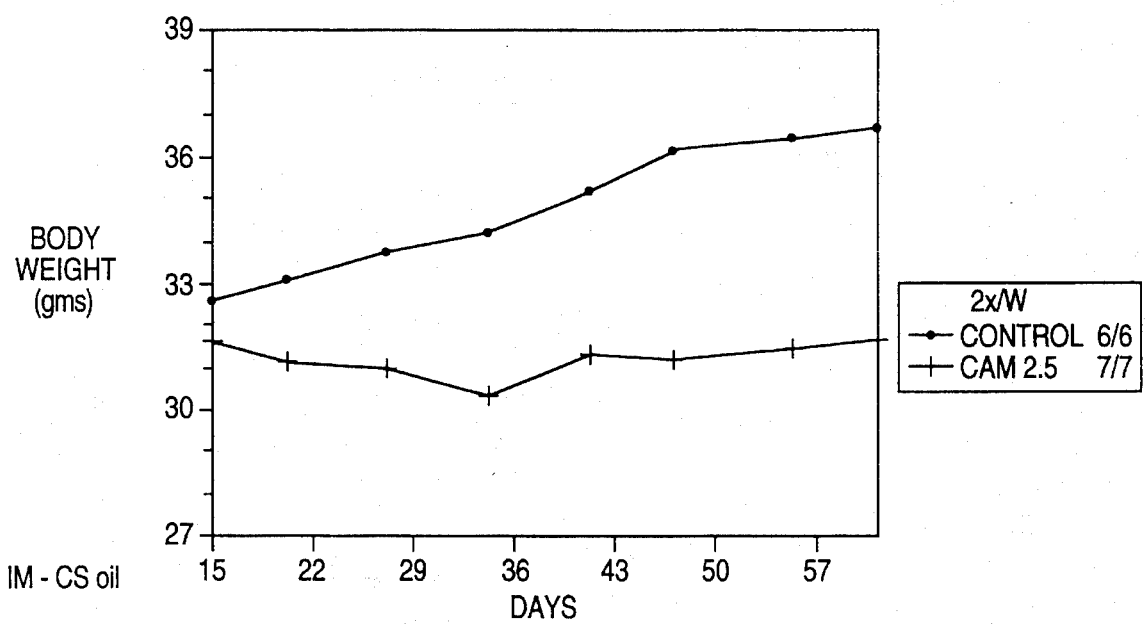

FIGS. 7a and 7b show the same results for human pancreatic cancer.

Figure 8A:
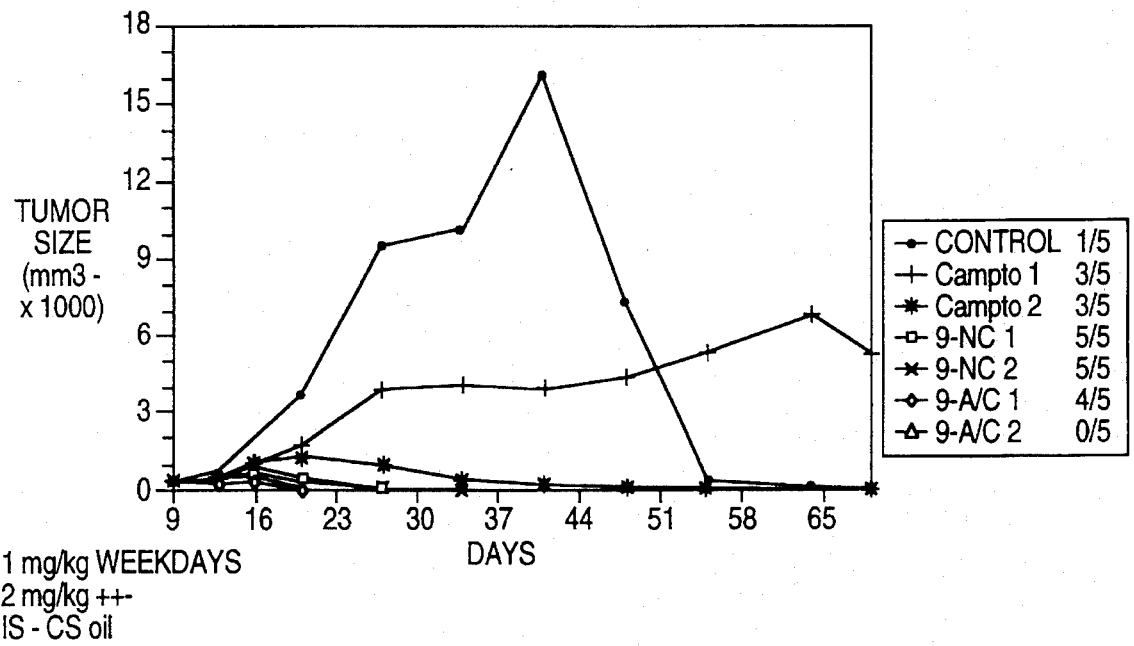
FIGS. 8a and 8b show the same results for human melanoma cancer.
Figure 8B:
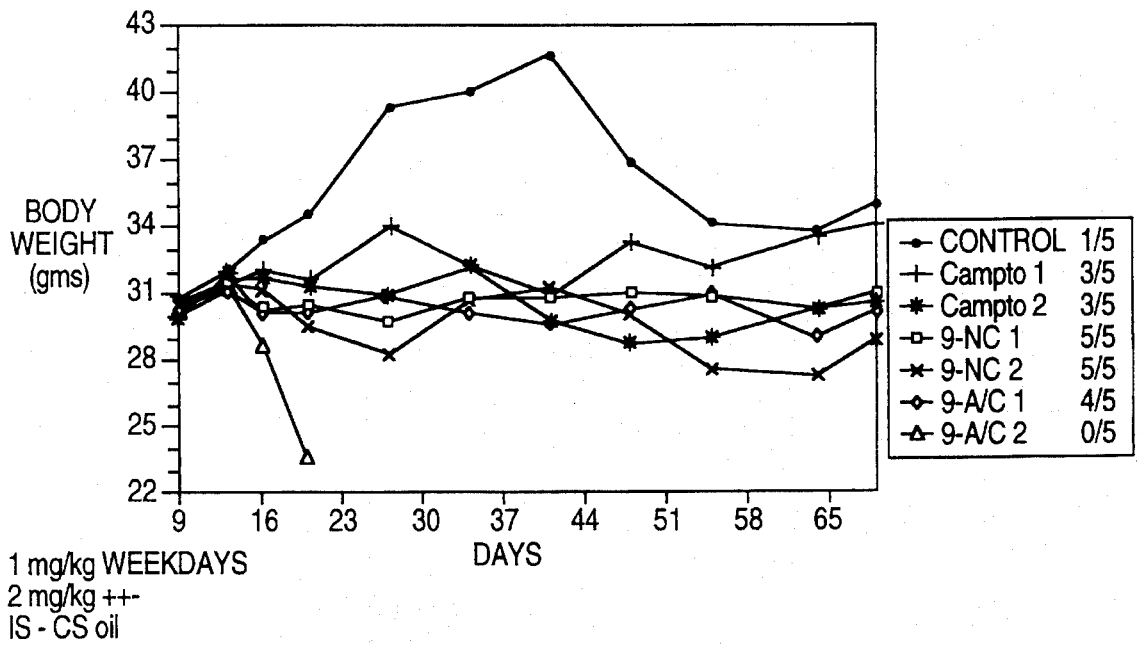

FIGS. 8a and 8b show the same results for human melanoma cancer.

It is clear from these studies, that purified CPT with the closed lactone ring have been demonstrated to possess an astonishing level of anticancer activity. This applies both to the spectrum of tumors covered and to the quality of the responses. The CPT purified by the methods of the present invention has been able to block growth completely and to totally regress human xenografts of carcinomas (lungs, breast, colon, prostate, leukemia, osteosarcoma, pancreatic, bladder) and malignant melanomas. This has been accomplished without any observable toxicity.

Other embodiments of the present invention will be apparent to those skilled in the art from consideration of the specification and practice of the present invention disclosed herein. It is intended that the specification and examples be considered as exemplary only, with a true scope and spirit of the invention being indicated by the following claims.

What is claimed is:

1. A method of purifying 20(S)-comptothecin comprising the steps:

(1) derivatizing 20(S)-camptothecin in a starting natural plant material containing said 20(S)-camptothecin to a $C_{20}$ ester or ether of 20(S)-camptothecin wherein said ester or ether is more soluble in an organic solvent than said 20(S)-camptothecin, wherein said starting natural plant material containing 20(S)-camptothecin is selected from the group consisting of *Camptotheca acuminata, Mappie foetida Miers, Ophiorrhiza mungos,* and *Erratama heyneana;*

(2) purifying said ester or ether by chromatography; and (3) hydrolyzing said ester or ether back to said 20(S)-camptothecin.

2. The method of claim 1, wherein said ester is an acetate.

3. The method of claim 3, wherein said hydrolysing is accomplished by heating said ester or ether in an acid.

4. The method of claim 3, wherein said acid is aqueous sulfuric acid or acetic acid.

5. The method of claim 3, wherein said acid is aqueous sulfuric acid or acetic acid in the presence of HCl, HBr, or a mixture thereof.

6. The method of claim 3, wherein said 20(S)-camptothecin resulting from step (3) is crystallized.

7. The method of claim 3 wherein prior to step (2), an organic solvent is added to said ester or ether to create an organic phase containing said ester or ether and an aqueous phase, wherein said organic phase is separated from said aqueous phase.

* * * * *

UNITED STATES PATENT AND TRADEMARK OFFICE
CERTIFICATE OF CORRECTION

PATENT NO. : 5,527,913
DATED : June 18, 1996
INVENTOR(S) : Hellmuth R. HINZ

It is certified that error appears in the above-identified patent and that said Letters Patent is hereby corrected as shown below:

In column 12, claim 3, line 15, "hydrolysing" should read --hydrolyzing--.

In column 12, claim 6, line 22, "claim 3" should read --claim 1--.

In column 12, claim 7, line 24, "claim 3" should read --claim 1--.

Signed and Sealed this

Third Day of September, 1996

Attest:

BRUCE LEHMAN

Attesting Officer     Commissioner of Patents and Trademarks